US 6,635,467 B2

(12) United States Patent
Chen et al.

(10) Patent No.: US 6,635,467 B2
(45) Date of Patent: Oct. 21, 2003

(54) *MONASCUS PURPUREUS* MUTANT AND ITS USE IN PREPARING YELLOW PIGMENT

(75) Inventors: Yen-Lin Chen, Hsinchu (TW); Ing-Er Hwang, Hsinchu (TW); Ming-Chih Lin, Hsinchu (TW); Ting-Kuo Huang, Hsinchu (TW); Chien-Cho Chen, Hsinchu (TW); Gwo-Fang Yuan, Hsichu (TW)

(73) Assignee: Food Industry Research and Development Institute (TW)

( * ) Notice: Subject to any disclaimer, the term of this patent is extended or adjusted under 35 U.S.C. 154(b) by 10 days.

(21) Appl. No.: 09/938,958

(22) Filed: Aug. 24, 2001

(65) Prior Publication Data

US 2002/0061547 A1 May 23, 2002

(30) Foreign Application Priority Data

Sep. 29, 2000 (CN) .......................................... 89120237 A

(51) Int. Cl.$^7$ ............................. C12N 1/00; C12N 1/14; C12P 1/00
(52) U.S. Cl. ...................... 435/243; 435/41; 435/254.1; 435/911
(58) Field of Search ...................... 435/41, 243, 254.1, 435/311

(56) References Cited

U.S. PATENT DOCUMENTS

| 4,442,209 A | 4/1984 | Miyake et al. |
| 5,429,943 A | 7/1995 | Kim et al. |
| 5,457,039 A | 10/1995 | Kim et al. |

FOREIGN PATENT DOCUMENTS

| JP | 07274978 A | * 10/1995 |

OTHER PUBLICATIONS

CBS Fungi database (cbs.knaw.nl/scripts/ CBSFungi .dll).*
Ayres et al. 1980, Microbiology of Foods, W.H. Freeman and Company, San Francisco, p. 199.*

* cited by examiner

Primary Examiner—Christopher R. Tate
Assistant Examiner—Kailash C. Srivastava
(74) Attorney, Agent, or Firm—LaRiviere, Grubman & Payne, LLP

(57) ABSTRACT

The invention relates to a mutant of *Monascus purpureus*, designated as *Monascus purpureus* M011, which is useful in the production of yellow pigments with a low amount of citrinin.

1 Claim, No Drawings

MONASCUS PURPUREUS MUTANT AND ITS USE IN PREPARING YELLOW PIGMENT

FIELD OF THE INVENTION

The invention provides a mutant of *Monascus purpureus;* and its use in preparing yellow pigments.

BACKGROUND OF THE INVENTION

Historically, the genus Monascus has been wildly used as food additives in China and other Asiatic contries. U.S. Pat. Nos. 4,442,209, and 5,457,039 have disclosed the utilization of Monascus sps. in the production of red, yellow and orange pigments which are served as the major sources of natural pigments. According to U.S. Pat. No. 5,429,943, the ratios between the red and yellow pigments among the Monascus pigments are mostly 1:1, and the hue of the Monoscus pigments shows red. Therefore, the Monascus pigments are useful in the production of red pigments. The relevant prior art references disclosing the utilization of genus Mocascus in the production of Monascus yellow pigments include: U.S. Pat. No. 5,013,564, wherein a reduction reaction is used to treat Monoscus pigments; and JP 55088696 and 81053589, wherein the cultural conditions, such as pH value or cultural medium, are controlled to achieve the purpose of producing Monascus yellow pigments.

Blanc et. al. (International Journal of Food Microbiology; 27, (1995), 201–213) found that Monascus sps. were capable of producing a fungal toxin (citrinin), which received considerable attention to the safety of the Monascus pigments. JP 7274978 discloses a method to reduce the amount of citrinin (lower than 1 ppm) by a mutant strain. However the pigments produced by the method are mostly red pigments and the yellow pigments can only be obtained by an additional processing treatment. Although Monascus sps have been widely used in the production of red pigments, a Monascus strain which could produce a higher proportion of yellow pigments and a lower amount of citrinin had not been found until now.

SUMMARY OF THE INVENTION

The present invention provides a mutant of *Monascus purpureus* designated as *Monascus purpureus* M011, or the mutant thereof, which can produce yellow pigments directly in a solid or liquid medium using cheap natural raw materials without any further processing steps, and a very low amount of citrinin produced thereby.

The invention also provides a method for producing yellow pigments by using the novel mutant or mutants thereof of the present invention.

The invention further provides a yellow pigment composition, containing a low amount of citrinin, prepared by the novel mutant of the present invention or mutants thereof

DETAILED DESCRIPTION OF THE INVENTION

The present invention provides a mutant of *Monascus purpureus* designated as *Monascus purpureus* M011, which is obtained by mutagenizing *Monascus purpureus* CCRC 31499 (also named as *Monascus anka* ATCC 16360, CBS 283.34, IFO 4478, and KFCC 11832) and screening therefrom.

*Monascus purpureus* CCRC 31499 is available from the Food Industry Research and Development Institute (FIRDI) in Hsin-Chu, Taiwan. The invention further comprises the mutants of *Monascus purpureus* M011 of the present invention, which can be prepared by using any conventional relevant mutation techniques, e.g., treating with chemical or physical mutagens (such as UV light, X-ray, or γ-ray) and chemical substances (such as N-methyl-N'-nitro-N-nitrosoguanidine).

The strain of *Monascus purpureus* M011 of the invention has been deposited in the Food Industry Research and Development Institute, Taiwan, on Sep. 18, 2000, and assigned the accession No. CCRC 930045; and has also been deposited with the American Type Culture Collection, (ATCC, 10801 University Boulevard, Manassas, Va. 20110-2209, USA) on Sep. 22, 2000 in accordance with the Budapest Treaty, and assigned the accession No. ATCC PTA-2496.

According to the present invention, the method for producing yellow pigments by using *Monascus purpureus* M011 or a mutant thereof can be performed by fermentation in a solid or liquid cultural medium.

According to the present invention, all known as carbon and nitrogen sources can be used in the above medium. Natural material is the preferred embodiment of the invention, wherein the carbon source includes, but not limited to rice powder, corn starch, rice starch, wheat starch, glucose, maltose, sucrose, and glycerol, or combination thereof; and the nitrogen source includes, but is not limited to soybean powder, soybean albumen, digestive albumen, yeast extract, corn steep liquor, glutamic acid, ammonium chloride, and potassium nitrate, or combination thereof.

According to one preferred production method of the present invention, the pH of the cultural medium is from 2 to 8.

According to the present invention, the amount of citrinin in the yellow pigment fermentation products is less than 1 ppm, preferably less than 0.3 ppm, and most preferably less than 0.2 ppm.

According to the present invention, the produced yellow fermentation liquid is useful as an additive to food. The yellow pigments in the fermentation liquid can be purified by various conventional techniques, e.g., the ionic exchange method as taught in IP 07216248, the method by controlling the solvent and pH values as taught in JP 61281158, and the ethanol purification methods used in JP 54033535, 53069887, and 52034985. In addition, yellow pigments can be extracted from fungi by conventional techniques, e.g., the method taught in JP 03254686. The yellow pigments fermentation liquid of the present invention can be used as additives for example, to food, cosmetics and pharmaceutical products, after a further purification process.

The following examples are used for illustration, but not for limiting the invention.

EXAMPLE 1

General Analysis Methods (1) Analysis of Yellow and Red Pigments

Fermentation liquid of the strain was diluted properly, and the $OD_{400}$ and $OD_{500}$ values of the diluted liquid were determined at 400 and 500 nm by the spectrophotometer for the yellow and red pigments, respectively. The ratios of the readings of $OD_{400}$ to $OD_{500}$ were used to determine the quality of the yellow pigments, i.e. a higher value of the ratio represents a higher proportion of the yellow pigments.

(2) Quantitative analysis of Citrinin

The following HPLC analysis procedures were used to determine the amount of citrinin in fermentation liquid of the strain. The fermentation liquid (7 ml) was adjusted to pH 3.5 and then incubated for 1 hour. Three (3) ml of ethyl acetate were added into the liquid and, 30 min later, the ethyl acetate layer was collected. The steps of addition and collation ethyl acetate were repeated twice. The collected ethyl acetate was then dried.

The dried sample was dissolved in methanol (1 ml), and then sieved through a membrane with a pore size of 0.2 $\mu$m. Ten (10) $\mu$l of the filtrate was applied for the HPLC analysis under the following conditions:

| | |
|---|---|
| Column: | $\mu$ Bondapak $C_{18}$ (10 $\mu$m, Waters) |
| Flow rate: | 1.0 ml per minute |
| Detector: | UV detector (Waters photodiarray assay 966, analysising wave 225–345 nm) |
| Mobile phase (gradient): | 0.8% phosphoric acid: acetonitrile: 2-propanol is from 60:35:5 to 25:70:5 |
| Run time: | 20 min |
| Retention time: | 11 min |

The concentrations of citrinin were calculated by comparing the values of the detected samples with that of the standard (Sigma).

EXAMPLE 2

Mutagenesis and Screening of the Mutant of the Invention

*Monascus purpureus* strain CCRC 31499 was inoculated onto a PDA (infusion from potato 20%, Dextrose 2%, and agar 2%) slant, and incubated at 30° C. for 7 days. The spores were washed off with sterile water from the slants. The collected spore suspension (over $10^7$ spores per ml) was irradiated with UV light for 2 mm. After a serial dilution, the diluted spore suspension samples were spread onto PDA plates and incubated at 30° C. for 2 to 3 days. The colonies showing yellowish orange were selected for conducting a mutant stability test performed in the medium containing rice powder (60 g/l), soybean powder (30 g/l), and $MgSO_4.7H_2O$ (5 g/l).

Each stable mutant was inoculated onto a PDA slant and incubated at 30° C. for 7 days. The spores of each mutant were washed off with sterile water. Each spore suspension ($5 \times 10^5$) was transferred to a 250 ml flask containing 50 ml of the above medium and incubated at 30° C. with shaking at 150 rpm for 5 to 7 days. The fermentation liquid of each mutant was collected and determined the absorbance at $OD_{400}$ and $OD_{500}$, from which the mutants having a higher ratio of $OD_{400}$ to $OD_{500}$ were selected. Finally, a stable mutant, designated as *Monascus purpureus* M011, having the $OD_{400}$ and $OD_{500}$ values of 6.1 and 1.9, respectively, was chosen. The morphologic characterization of the mutant is shown as follows.

CYA Medium (Per Liter Contains Sucrose 30 g, $NaNO_3$ 3 g, $K_2HPO_4$ 1.0 g, $MgSO_4$ 0.5 g, KCl 0.5 g, $FeSO_4$ 0.01, and Yeast Extract 1 g)

After an incubat on period of for 7 days, the colonies showed light orange in color with the size of 25–26 mm. After incubating for 10 days, the aerial mycelium was white; the colonies showed light yellowish orange, and 30–32 mm in size, and the air-borne mycelium was white. Conidiophores were various in length, and branches thereon were irregular and maintained as colorless. Conidiospore showed a pear shape. One or two spores formed a string. The size of conidiospore was 7–11 (–16)×8–12 (–17) $\mu$m, and many of the spores were extra large conidiospores. However, in CYA medium, only conidiospores were found, but without ascorcarps.

MEA Medium (Per Liter Contains Malt Extract 20 g, Peptone 1 g, Glucose 20 g, and Agar 15 g)

After an incubating on period of 7 days, the colonies showed vivid orange in color with the size of 30–32 mm. After incubating for 10 days, the colonies showed orange in color with the size of 29–30 mm. Both conidiospores and ascocarp were colorless. Some red-brown conidiospore-like spherical spores were found in the medium. The ascocarps were 40–50 $\mu$m in size; and the ascospores were oval-shaped (5×6–7 $\mu$m).

G25N Medium (Per Liter Contains $K_2HPO_4$ 0.75 g, Czapek Concentrate 7.5 ml, Yeast Autolysate or Extract 3.7 g, Glycerol 250 g, Agar 12 g, and Water 750 ml)

After an incubation period of for 7 days, white macrogrowths were found in the medium. After incubating for 10 days, the colonies showed orange in color with the size of 12–14 mm.

The comparison between *Monascus purpureus* mutant strain M011 and the parental strain CCRC 31499 is shown in Table 1.

TABLE 1

| | Parental strain CCRC 31499 | Mutant strain M011 |
|---|---|---|
| Size of conidiospore[a] | 8–12 × 10–13 mm | 7–11 × 8–12 mm |
| Size of ascocarp[a] | 37–45 mm | 40–50 mm |
| Size of ascospore[a] | 4–5 × 5–6 mm | 5 × 6–7 mm |
| $OD_{400}$[b] | 2.35 | 35.48 |
| $OD_{500}$[a] | 1.88 | 5.85 |
| $OD_{400}/OD_{500}$ | 1.25/1 | 6/1 |
| Citrinin[b] | 1.1 ppm | 0.24 ppm |
| $OD_{400}$[b] | 5.74 | 10 |
| $OD_{500}$[a] | 8.15 | 0.78 |

[a]incubated in CYA medium.
[b]incubated at 30° C. with shaking at 150 rpm for 5 days in the medium containing rice powder 60 g/l, glutamic acid 30 g/l, $MgSO_4.7H_2O$ 5 g/l, KCl 0.5 g/l, $KH_2PO_4$ 1 g/l, $ZnSO_4.7H_2O$ 10 mg/l, $MnSO_4.H_2O$ 10 mg/l and $FeSO_4.7H_2O$ 10 mg/l.
[c]incubated at 30° C. with shaking at 150 rpm for 5 days in the medium containing rice powder 60 g/l, glutamic acid 30 g/l, and $MgSO_4.7H_2O$ 4.8 mg/l at pH 6.25.

EXAMPLE 3

Carbon Sources for the Production of Yellow Pigments

According to the method described in EXAMPLE 2, the spores of the *Monascus purpureus* mutant strain M011 were inoculated in the mediums containing carbon source 60 g/l, glutamic acid 30 g/l, $MgSO_4.7H_2O$ 5 g/l, KCl 0.5 g/l, $KH_2PO_4$ 1 g/l, $ZnSO_4.7H_2O$ 10 mg/l, wherein each of rice powder, corn starch, rice starch, wheat starch, glucose, maltose, sucrose, or glycerol were used as the carbon source. The cultivations were incubated at 30° C. with shaking at 150 rpm for 5 days. The fermentation liquid samples were collected, and the values of $OD_{400}$ and $OD_{500}$ and the amount of citrinin of the samples were determined. The results illustrated in Table 2 shown that *Monascus purpureus* mutant strain M011 cultivated in all of the different nature carbon sources produced a large proportion of yellow pigments, and the amount of citrinin was very low.

TABLE 2

| | $OD_{400}$ | $OD_{500}$ | $OD_{400}/OD_{500}$ |
|---|---|---|---|
| Rice powder | 9.475 | 3.068 | 3:1 |
| Cornstarch | 5.123 | 0.778 | 6:1 |
| Rice starch | 8.948 | 2.333 | 4:1 |
| Wheat starch | 6.823 | 0.828 | 7:1 |
| Glucose | 2.74 | 0.232 | 12:1 |
| Glycerol | 0.557 | 0.092 | 6:1 |
| Maltose | 1.718 | 0.173 | 10:1 |
| Sucrose | 1.76 | 0.227 | 8:1 |

*Each amount of the citrinin herein was below the detectable value 0.15 ppm.

EXAMPLE 4

Nitrogen Sources for the Production of Yellow Pigments

According to the method described in EXAMPLE 3, in a triplicate experiment, the values of $OD_{400}$ and $OD_{500}$ and the amount of citrinin in the fermentation liquid were determined, wherein rice powder was used as the carbon source and each of soybean powder, soybean albumen, digestive albumen, yeast extract, corn steep liquor, glutamic acid, ammonium chloride or potassium nitrate was used as the nitrogen source. Table 3 shows that the proportion of the yellow pigments produced by *Monascus purpureus* mutant strain M011 in different nitrogen sources was all very large, and the amount of citrinin was very low.

TABLE 3

| | $OD_{400}$ | $OD_{500}$ | $OD_{400}/OD_{500}$ | citrinin |
|---|---|---|---|---|
| Soybean powder | 3.49 | 0.9 | 4:1 | 0.178 |
| Soybean albumen | 2.19 | 0.42 | 5:1 | 0 |
| Digestive albumen | 2.62 | 0.47 | 5;1 | 0 |
| Yeast extract | 2.8 | 0.55 | 5:1 | 0 |
| Corn steep liquor | 2.56 | 0.43 | 5:1 | 0 |
| Glutamic acid | 3.5 | 0.62 | 6:1 | 0.209 |
| Ammonium chloride | 0.859 | 0.215 | 4:1 | 0 |
| Potassium nitrate | 1.96 | 0.38 | 5:1 | 0 |

"0" represents the amount of citrinin was below 0.15 ppm.

EXAMPLE 5

The pH Value for the Production of Yellow Pigments

According to the method described in EXAMPLE 3, in triplicate experiments, the values of $OD_{400}$ and $OD_{500}$ of each fermentation liquid were determined, wherein the mutant strain was cultivated in the medium containing rice powder 60 g/l, glutamic acid 30 g/l, $MgSO_4.7H_2O$ 4.8 g/l, and KCl 0.5 g/l in the conditions of various initial pH values. Table 4 shows the results that *Monascus purpureus* mutant strain M011 cultivated in both acid and basic conditions was able to produce a large proportion of yellow pigments.

TABLE 4

| | $OD_{400}$ | $OD_{500}$ | $OD_{400}/OD_{500}$ |
|---|---|---|---|
| pH 2.73 | 3.38 | 0.76 | 5:5:1 |
| pH 3.87 | 3.19 | 0.62 | 5:1 |
| pH 5.01 | 10.69 | 1.62 | 6:1 |
| pH 5.86 | 35.47 | 5.91 | 6:1 |
| pH 6.25 | 35.13 | 6.02 | 6:1 |
| pH 6.9 | 28.83 | 2.83 | 10:1 |
| pH 7.45 | 18.93 | 2.74 | 7:1 |

What is claimed is:

1. A biologically pure culture of a mutant of the microorganism *Monascus purpureus* which is designated as *Monascus purpureus* M011, which is deposited with the American Type Culture Collection on Sep. 22, 2000, and assigned the accession No. ATCC PTA-2496.

* * * * *